US005773427A

United States Patent [19]
Day

[11] Patent Number: 5,773,427
[45] Date of Patent: Jun. 30, 1998

[54] PREVENTION OF FIBER-INDUCED INTESTINAL GAS PRODUCTION BY CHITOSAN

[76] Inventor: Charles E. Day, 1224 Bear Creek Rd., Leitchfield, Ky. 42754

[21] Appl. No.: 656,577

[22] Filed: May 31, 1996

[51] Int. Cl.$^6$ .......................... A61K 31/73; A61K 31/715
[52] U.S. Cl. ................................. 514/55; 514/54; 514/57; 514/58; 514/59; 514/60; 514/824
[58] Field of Search ................................. 514/54, 55, 57, 514/58, 59, 60, 824

[56] References Cited

U.S. PATENT DOCUMENTS

| | | | |
|---|---|---|---|
| 3,257,275 | 6/1966 | Weisberg et al. | 424/653 |
| 4,223,023 | 9/1980 | Furda | 424/180 |
| 4,824,672 | 4/1989 | Day | 424/195.1 |
| 4,883,788 | 11/1989 | Day | 514/57 |
| 5,034,378 | 7/1991 | Cox | 514/23 |
| 5,380,522 | 1/1995 | Day | 424/78.08 |
| 5,453,282 | 9/1995 | Kanauchi et al. | 424/464 |
| 5,545,414 | 8/1996 | Behr et al. | 424/484 |

OTHER PUBLICATIONS

FDA/CFSAN Dietary Supplement Health and Education Act of 1994. http://vm.cfsan.fda.gov/~dms/dietsupp.html Dec. 1, 1995.

M.J. Koruda, Dietary fiber and gastrointestinal disease. Surg. Gynecol. Obstret. 177:209–214 (1993), month not available.

J. Tomlin, C. Lowis, and N.W. Read. Investigation of normal flatus production in healthy volunteers. Gut 32:665–669 (1991), month not available.

E.W. Hellendoorn. Fermentation as the principal cause of the physiological activity of indigestible food residue. In: Topics in Dietary Fiber Research ed. by G.A. Spiller and R.J. Amen. Plenum Press, New York, NY, pp. 127–168 (1978), month not available.

T.G. Ganiats, W.A. Norcross, A.L. Halverson, P.A. Burford, and L.A. Palinkas. Does Beano prevent gas? A double–blind crossover study of oral α–galactosidase to treat dietary oligosaccharide intolerance. J. Fam. Pract. 39:441–445 (1994), month not available.

M. Sugano, T. Fujikawa, Y. Hiratsuji, and Y. Hasegawa. Hypocholesterolemic effects of chitosan in cholesterol–fed rats. Nutr. Rep. Internat. 18:531–537 (1978), month not available.

Y. Maezaki, K. Tsuji, Y. Nakagawa, Y. Kawai, M. Akimoto, T. Tsugita, W. Takekawa, A. Terada, H. Hara, and T. Mitsouka. Hypocholesterolemic effect of chitosan in adult males. Biosci. Biotech Biochem. 57:1439–1444 (1993), month not available.

Y. Fukada, K. Kimura, and Y. Ayaki. Effect of chitosan feeding on intestinal bile acid metabolism in rats. Lipids 26:395–399 (1991), month not available.

S. Aoe, H. Oda, and K. Tatsumi, Water–soluble dietary fiber–chitosan complexes for use in food. Jpn. Kokai Tokkyo Koho JP 05 86,227 [93,86,227]. (Chem. Abstr. 119:141508 (1993)), month not available.

A.H.M. Ross, M.A. Eastwood, W.G. Brydon, J.R. Anderson, and D.M.W. Anderson. A study of the effects of dietary gum arabic in humans. Amer. J. Clin. Nutr. 37:368–375 (1983), month not available.

J.L. Nelson, J.W. Alexander, L. Gianotti, C.L. Chalk, and T. Pyles. Influence of dietary fiber on microbial growth into vitro and bacterial translocation after burn injury in mice Nutrition 10:32–36 (1994), month not available.

L.A. Hadwiger, T. Ogawa, and H. Kuyama. Chitosan polymer sizes effective in inducing phytoalexin accumulation and fungal suppression are verified with synthe–sized oligomers. Mol. Plant Microbe Interact. 7:531–533 (1994), Abstract only, month not available.

A. Terada, H. Hara, D. Sato, T. Higashi, S. Nakayama, K. Tsuji, K. Sakamoto E. Ishioka, Y. Maezaki, T. Tsugita, T. Takekawa and T. Mtsuoka. Effect of dietary chitosan on faecal microbiota and faecal metabolites of humans. Microb. Ecol. Health Dis. 8:15–21 (1995), Abstract only, month not available.

M. Meshali and K., Gabr. International Journal of Pharmaceutics (Amsterdam) 89(3) 177–181 (1993), month not available.

M. Tanaka, T. Toshima, and K. Tatsumi, Manufacture of dietary fiber–rich expanded foods with chitosan. Jpn. Kokai Tokkyo Koho JP 03 262 461 [91,262,461]. (Chem. Abstr. 116:104868$\mu$ (1992)) month not available.

Primary Examiner—Kathleen K. Fonda
Attorney, Agent, or Firm—The Firm of Gordon W. Hueschen

[57] ABSTRACT

The tendency of an orally-ingestible dietary fiber composition to cause excessive flatulence upon oral administration is reduced considerably by the incorporation therein, in addition to other dietary fiber components, a flatulence-reducing amount of chitosan, or by administering such a flatulence-reducing amount of chitosan concurrently with the other dietary fiber components, illustratively the usual antihyperlipidemic pharmaceutical dietary fiber composition or dietary supplement composition. A preferred dietary fiber composition according to the invention incorporates a plurality of dietary fiber components other than chitosan, preferably acacia gum, pectin, and guar gum, together with a flatulence-reducing amount of chitosan.

18 Claims, No Drawings

5,773,427

PREVENTION OF FIBER-INDUCED INTESTINAL GAS PRODUCTION BY CHITOSAN

BACKGROUND OF THE INVENTION

1. Field of the Invention

Dietary fiber consumption and therapy with dietary fiber compositions, amelioration of flatulation effects arising therefrom by the employment of a flatulation-reducing amount of chitosan in admixture or concurrently with other dietary fibers, and certain dietary fiber compositions incorporating a flatulation-reducing amount of chitosan.

2. Background of the Invention and Prior Art

Dietary fiber consumption offers protection from a variety of diseases including coronary artery disease, constipation, diverticulosis, appendicitis, obesity, diabetes, and colon cancer (1). Because of the widespread recognition of its many healthful benefits, a plethora of food products and dietary supplements is readily available to the consumer and is widely utilized. Also, increased consumption of fresh fruits, whole grains, beans, and vegetables, high in dietary fiber content, is widely recommended by most health authorities. The recommended daily value (DV) for dietary fiber consumption in this country is currently thirty (30) grams per day for an adult. Dietary fiber formulations useful for the control of serum cholesterol concentrations and for reducing the risk of coronary artery disease (2,3) have been developed previously.

In addition to their many healthful benefits, dietary fibers also cause some undesirable side effects, primarily increased intestinal gas formation which can induce socially embarrassing and/or malodorous flatulence as well as bloating, abdominal pains and discomfort (4,5). Unfortunately, nothing is presently available to effectively prevent intestinal gas formation induced by a wide variety of dietary fibers. α-Galactosidase enzyme preparations are widely used to prevent intestinal gas formation caused by ingesting beans and various other legumes. These preparations are effective since they digest the galactose-containing oligosaccharides found in beans, which are the primary cause for the gas production (6). However, such enzyme preparations are not useful for preventing intestinal gas production brought about by increased dietary fiber consumption. Because of the increased consumption of foods and dietary supplements enriched with various dietary fibers, a growing need exists to find effective methods and means for controlling intestinal gas production induced by dietary fibers when ingested by a person for whom such gas production would cause a problem and hence inhibit or curtail their use and consequent healthful benefits thereof.

Chitosan is a natural fiber which consists of a high molecular weight polymer of glucosamine and which occurs in many species of fungi. It is produced commercially by the deacetylation of chitin, which is the primary component of the exoskeletons of arthropods such as the crustaceans shrimp and crab as well as most insects. Chitosan derived from chitin, a waste by-product of shrimp and crab processing, has many industrial as well as biomedical applications. Chitosan can reduce serum cholesterol in both experimental animals and human patients (7,8) which may be mediated in part by modulation of bile acid metabolism (9). It also inhibits lipid absorption and has been patented as "a method of reducing lipid absorption in mammals which comprises orally administering to the mammal an amount of chitosan effective to substantially reduce the lipid absorption" (10). A combination of chitosan with ascorbic acid (vitamin C) has been patented as "a method of reducing obesity in a mammal to be treated, said method comprised of administering to the mammal amounts of chitosan and sodium ascorbate effective to treat obesity in said mammal, said chitosan inhibiting digestion and absorption of the lipid into the mammal and said sodium ascorbate enhancing the inhibitory activity of the chitosan" (11). Chitosan has been mixed with several water-soluble fibers such as pectins, guar gum, locust bean gum, konnyaku mannan, and carrageenan to produce complexes with modified physico-chemical characteristics useful in the preparation of various foods (12).

The Present Invention

Acacia gum (gum arabic) is a water-soluble dietary fiber composed of a very high molecular weight, complex, acidic heteropolysaccharide. Like many other dietary fibers, such as guar gum, psyllium hydrocolloid and pectin, it reduces serum cholesterol in human patients and at the same time increases intestinal gas production (13). Based on considerations such as cost, biological activity, and desirable physico-chemical properties, a dietary fiber mixture, for reducing serum cholesterol concentrations in human patients, of which acacia gum may be and preferably is the single largest component, has now been formulated. To this dietary fiber mix for lowering cholesterol levels, pectin, guar gum, and chitosan also are added for greater effectiveness, especially since the exact mechanism of the hypocholesterolemic effect of the plurality of dietary fibers will differ and the mechanism, especially of this latter basic and positively charged natural polymer chitosan, may differ from that of the acidic and negatively-charged acacia gum polymer and from the guar gum and pectin. If the plurality of natural fibers do in fact exert their respective hypocholesterolemic activities via different mechanisms, then the possibility exists for a more than additive hypocholesterolemic response above what each fiber could produce by itself. To my knowledge no one has in the past reported mixing a plurality of dietary fibers plus chitosan, and especially these particular fibers, for any purpose, although chitosan-pectin and chitosan-acacia complexes have been used as tablet matrices for delivery of chlorpromazine (14), swollen chitosan has been admixed with corn bran and various nutrients to provide dietary fiber-rich expanded foods (15), and chitosan-pectin has been suggested for use in treating irritable bowel syndrome (16). The goal of the formulation of the mixture of acacia gum, pectin, guar gum, and chitosan as set forth in Example 1 was therefore fundamentally to produce a more effective dietary fiber formulation for reducing serum cholesterol levels. From this original concept, a preferred mixture of dietary fibers for hypocholesterolemic activity and use evolved into a mixture of a plurality of dietary fibers other than chitosan, plus a flatulence-reducing amount of chitosan, since the effectiveness of a mixture of dietary fibers other than chitosan does in fact produce more than an additive hypocholesterolemic response above what each fiber could produce by itself in view of the fact that each dietary fiber acts and exerts its effect through its own particular mechanism, whereas the chitosan, in addition to acting as a usual dietary fiber, also imparts a reduction in flatulence to the dietary fiber mixture, as will be further disclosed hereinafter, so that the preferred composition of the invention involves an admixture of a plurality of dietary fibers other than chitosan plus a flatulence-reducing amount of chitosan, as will become apparent hereinafter.

Patients who ingested a fiber mixture similar to that set forth in Example 1, but without any chitosan, exhibited the usual symptoms of intestinal gas formation caused by increased fiber consumption. These symptoms included increased flatulence, bloating, and abdominal distension, pain, and general discomfort. When chitosan was added to the acacia, pectin, and guar gum fiber mixture, as in Example 1, for the purpose of enhancing its cholesterol effect, it was unexpectedly discovered that the usual symptoms of fiber-induced intestinal gas formation did not appear. Therefore, irrespective of its effects on cholesterol-lowering activity, the mixture of chitosan with the other dietary fibers produced a more patient-acceptable dietary fiber formulation by substantially alleviating, preventing, or eliminating the troublesome gastrointestinal side effects of the other fibers, and such has been found to be the case whatever the other dietary fibers may be (besides chitosan).

The mechanism by which chitosan prevents symptoms of other fiber-induced intestinal gas formation is presently unknown. It is not known whether chitosan reduces intestinal gas production per se induced by dietary fiber or whether it simply prevents the symptoms of such production, possibly by dispersing or entrapping the gas so produced. The human gastrointestinal tract, especially the colon, contains a myriad of species of microflora. It is possible that chitosan could be preventing symptoms of gas production by preventing the actual production of intestinal gas via an antimicrobial effect on certain gas-producing microorganisms in the human gastrointestinal tract, since chitosan has been shown to inhibit the growth of some microorganisms (17,18). However, based on the information available, it is impossible to explain the effect discovered and herein reported which is the basis of the present invention. It is presently unknown whether a relationship exists between any reputed antimicrobial activity of chitosan and its prevention of gastrointestinal side effects induced by dietary fiber consumption by human patients. However, present evidence demonstrates that dietary chitosan causes no detectable change in the concentration of short-chain fatty acids, an indicator of microbial activity in the colon (19). These data strongly indicate that no relationship exists between the prevention of symptoms of intestinal gas production by dietary chitosan and its in vitro antimicrobial activity. Therefore, the present invention was totally unexpected, and its mechanism remains unexplained.

OBJECTS OF THE PRESENT INVENTION

It is a principal object of the present invention to provide novel dietary fiber compositions for oral administration which produce diminished flatulation upon oral administration, a method of preparing the same, and a method of diminishing the normal tendency to excessive flatulation produced upon ingestion of dietary fiber compositions by the administration, in addition to other dietary fiber components, of an effective flatulation-reducing amount of chitosan either in admixture with other dietary fiber components or concurrently therewith. It is a further object of the invention to provide effective dietary fiber compositions for reducing serum cholesterol levels which incorporate therein, in addition to other dietary fiber components, an effective flatulence-reducing amount of chitosan. A particular object of the invention is the provision of such compositions containing acacia gum, pectin, and guar gum and, in addition thereto, an effective flatulence-reducing amount of chitosan. Other objects of the invention will become apparent hereinafter and still others will be obvious to one skilled in the art to which this invention pertains.

SUMMARY OF THE INVENTION

What I believe to be my invention, then, inter alia, comprises the following, singly or in combination:

A method of reducing flatulence which results upon oral ingestion by a human being of an orally-ingestible dietary fiber other than chitosan comprising the step of admixing a flatulence-reducing amount of chitosan with the dietary fiber other than chitosan before oral administration thereof; such a method wherein the dietary fiber other than chitosan is selected from the group consisting of acacia gum, pectin, guar gum, beta-glucan, fruit fibers, vegetable fibers, legume fibers, psyllium, plantago, xanthan, agar, alginic acid, cellulose gum, methylcellulose, agarose, dextran, tragacanth, karaya, glucomannan, locust bean, konnyaku mannan, and carrageenan; such a method wherein a plurality of dietary fibers other than chitosan are employed; such a method wherein the weight ratio of chitosan, which is admixed with other dietary fibers, to the other dietary fibers is between about 1:20 and about 10:1; such a method wherein the weight ratio of chitosan to other dietary fibers is between about 1:17 and about 3:1; such a method wherein the weight ratio of chitosan to other dietary fibers is between about 1:10 and about 1:4; such a method wherein the percent by weight of chitosan in the total dietary fiber admixture is between about 5 and about 90; such a method wherein the percent by weight of chitosan in the total composition is between about 10 and about 60; such a method wherein the percent by weight of chitosan in the total composition is between about 10 and about 25; and also a method of reducing flatulence which results upon oral ingestion by a human of an orally-ingestible dietary fiber other than chitosan comprising the step of orally administering a flatulence-reducing amount of chitosan in admixture with or concurrently with the dietary fiber other than chitosan; such a method wherein the weight ratio of chitosan to other dietary fibers administered is between about 1:20 and about 10:1; such a method wherein the weight ratio of chitosan to other dietary fibers is between about 1:17 and about 3:1; such a method wherein the weight ratio of chitosan to other dietary fibers is between about 1:10 and about 1:4; such a method wherein the percent by weight of chitosan to the total amount of dietary fiber composition administered is between about 5 and about 90; such a method wherein the percent by weight of chitosan to the total amount of dietary composition administered is between about 10 and about 60; such a method wherein the percent by weight of chitosan to the total amount of dietary composition administered is between about 10 and about 25; such a method wherein the dietary fiber other than chitosan is selected from the group consisting of acacia gum, pectin, guar gum, beta-glucan, fruit fibers, vegetable fibers, legume fibers, psyllium, plantago, xanthan, agar, alginic acid, cellulose gum, methylcellulose, agarose, dextran, tragacanth, karaya, glucomannan, locust bean, konnyaku mannan, and carrageenan; and such a method wherein a plurality of dietary fibers other than chitosan are employed.

Moreover, an antihyperlipidemic pharmaceutical or dietary supplement composition comprising dietary fiber which produces reduced flatulence upon oral administration to a human being comprising a plurality of dietary fibers other than chitosan and a flatulence-reducing amount of chitosan, the said flatulence being reduced as compared with that produced upon oral administration of the same composition without the chitosan; such a composition wherein the dietary fiber other than chitosan is selected from the group consisting of acacia gum, pectin, guar gum, beta-glucan, fruit fibers, vegetable fibers, legume fibers, psyllium, plantago, xanthan, agar, alginic acid, cellulose gum, methylcellulose, agarose, dextran, tragacanth, karaya, glucomannan, locust bean, konnyaku mannan, and carrageenan; such a composition wherein the dietary fibers other than chitosan are selected from the group consisting of acacia gum, pectin, and guar gum; such a composition wherein the dietary fibers other than chitosan comprise acacia gum, pectin, and guar gum; such a composition wherein the weight ratio of chitosan to other dietary fibers is between about 1:20 and about 10:1; such a composition wherein the weight ratio of chitosan to other dietary fibers is between about 1:17 and about 3:1; such a composition wherein the weight ratio of chitosan to other dietary fibers is between about 1:10 and about 1:4; such a composition wherein the percent by weight of chitosan in the total composition is between about 5 and about 90; such a composition wherein the percent by weight of chitosan in the total composition is between about 10 and about 60; such a composition wherein the percent by weight of chitosan in the total composition is between about 10 and about 25; such a composition wherein the amount of acacia gum in the composition is between about 20 and 40% by weight, the amount of pectin is between about 10 and 30% by weight, the amount of guar gum is between about 10 and 30% by weight, and wherein the amount of chitosan is between about 5 and 25% by weight; and finally such a composition wherein the amount of acacia gum in the composition is about 30% by weight, the amount of pectin is about 20% by weight, the amount of guar gum is about 20% by weight, and the amount of chitosan is about 5–15% by weight.

GENERAL DESCRIPTION OF THE INVENTION

The dietary fibers employed according to the present invention may be any of the usual dietary fibers other than chitosan, including, for example, acacia gum, pectin, guar gum, wheat bran, oat bran, rice bran, barley bran, oat β-glucan (oat gum), fruit fibers such as apple, pear, and plum fibers, vegetable fibers such as carrot, beet, and tomato fibers, legume fibers such as soybean, kidney bean, garbanzo, and pea bean fibers, and the like, as well as various usual gums and hydrocolloids including psyllium, plantago, xanthan, agar, alginic acid, cellulose gum, methyl cellulose, agarose, dextran, tragacanth, karaya, glucomannan, locust bean gum, konnyaku mannan, and carrageenan.

In addition to one or more, preferably two or more, of the foregoing dietary fibers, either admixed therewith or orally administered concurrently therewith, is a flatulence-reducing amount of chitosan, which may thus be present in admixture with other dietary fibers or administered concurrently therewith, illustratively in a weight ratio of 1:20 to 10:1, and the amount of chitosan administered together therewith or admixed together therewith will generally range from about 5% by total weight of the composition to as much as 90% by weight of the total composition, with between about 5% and 25% by weight and 5–15%, e.g., 10%, by weight being considered the approximate optimum by weight of total composition, this amount usually being entirely satisfactory and hence preferred.

The composition may also contain anticaking and flow-enhancing ingredients, such as anhydrous dicalcium phosphate and anhydrous magnesium oxide, which were employed in the following examples. Other anticaking and flow-enhancing agents which can be used are too numerous to mention, but include for example tricalcium phosphate, and numerous others will be immediately apparent to one skilled in the art.

As sweeteners may be employed aspartame, sugar, fructose, xylitol, sorbitol, powdered honey, saccharin, acesulfame, stevioside, and the like. Aspartame was used as sweetener in all of the examples which follow.

As flavorings used in the following examples natural orange flavor, vanilla, and natural strawberry flavor were employed, although a wide range including any one or more of dozens of readily-available natural and artificial flavors can be used in their place.

According to the method of the present invention, it is only necessary that the flatulence-reducing amount of chitosan be admixed with the other dietary fibers to be employed in a composition of the invention prior to oral administration thereof for the usual purposes and effects, or that the same amount be ingested concurrently with the other dietary fibers or fiber combinations. The method of making a suitable dietary fiber composition of reduced flatulence involves the admixture of the flatulence-reducing amount of chitosan with the other dietary fibers to be employed. The method of reducing flatulence involves the ingestion of a flatulence-reducing amount of chitosan along with the other dietary fibers which are orally ingested, either in admixture therewith or concurrently therewith. Suitable formulations according to the present invention include all those formulations in which dietary fibers have already been orally administered, including powders, powdered drink mixes, tablets, capsules, granulates, and chewable wafers or tablets, and the art is replete with innumerable forms of dietary fiber compositions to which the flatulence-reducing amount of chitosan may be added according to the present invention or, alternatively, with which the flatulence-reducing amount of chitosan may be concurrently orally administered.

As is usual in the art, compositions according to the present invention may contain optional preservatives, sweeteners, or flavorants which may provide a more palatable dosage form and assist in long-term patient compliance, but in general such additional ingredients are optional. Additionally, vitamins and minerals may be included in the compositions of the present invention and beta-carotene and chromium polynicotinate are representative, although the exact selection of vitamin and mineral additaments to be included will be at the discretion of the formulator. In addition, physiologically-acceptable buffers or antacids may be incorporated in the dietary fiber composition at the option of the formulator.

DETAILED DESCRIPTION OF PREFERRED EMBODIMENTS OF THE INVENTION

The following Examples are given to illustrate the compositions and method of the present invention, but are not to be construed as limiting.

EXAMPLE 1

An effective antihypercholesterolemic and antihyperlipidemic composition comprising a mixture of acacia gum with chitosan and other dietary fibers

| Ingredient | Amount (parts/100) |
| --- | --- |
| Acacia gum | 30 |
| Pectin | 20 |
| Guar gum | 20 |
| Chitosan | 10 |
| Anticaking and flow-enhancing agents, i.e., anhydrous dicalcium phosphate and magnesium oxide | 9 |
| Flavors and sweeteners, i.e., aspartame and natural orange flavor | 11 |

The proportion of chitosan to other dietary fibers in this Example is 1:7 and the weight percentage of chitosan to total weight of the composition is 10%.

Other compositions based upon the same ingredients may have 20 to 40% by weight of acacia gum, 10 to 30% by weight of pectin, 10 to 30% by weight of guar gum and 5 to 25% by weight of chitosan, without detracting from the effectiveness of the composition as an antihyperlipidemic pharmaceutical or dietary supplement composition for oral use, and without detracting from the effectiveness of the chitosan, which is present in all cases in a flatulence-reducing amount, in effecting this desirable pharmacological result.

When granulated and mixed together and tabletted or filled into capsules, or suspended in water as a drink mix with or without a suitable suspending or emulsifying agent according to established knowledge of the art, the results upon oral administration by a human being produce a reduction in flatulence as compared to utilization of the same composition without the flatulence-reducing amount of chitosan, as evidenced under the heading "Pharmacology" hereinafter.

A part or all of the acacia gum, pectin, and guar gum may be replaced by another dietary fiber as set forth elsewhere herein, for example, by psyllium, xanthan, tragacanth, carrageenan, locust bean, fruit, or bran or other vegetable fibers.

EXAMPLE 2

Wheat bran mixture with chitosan

| Ingredient | Amount (parts/100) |
| --- | --- |
| Wheat bran powder | 75 |
| Chitosan | 5 |
| Anticaking and flow enhancing agents | 10 |
| Flavors and sweeteners | 10 |

The proportion of chitosan to other dietary fiber in this Example is 1:15 and the weight percentage of chitosan to total weight of the composition is 5 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 3

Oat bran mixture with chitosan

| Ingredient | Amount (parts/100) |
| --- | --- |
| Oat bran powder | 85 |
| Chitosan | 5 |
| Anticaking and flow enhancing agents | 3 |
| Flavors and sweeteners | 7 |

The proportion of chitosan to other dietary fiber in this Example is 1:17 and the weight percentage of chitosan to total weight of the composition is 5 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 4

Oat β-glucan extract mixture with chitosan

| Ingredient | Amount (parts/100) |
| --- | --- |
| Oat β-Glucan Extract (Nurture ® 1080) | 60 |
| Chitosan | 20 |
| Anticaking and flow enhancing agents | 8 |
| Flavors and sweeteners | 12 |

The proportion of chitosan to other dietary fiber in this Example is 1:3 and the weight percentage of chitosan to total weight of the composition is 20 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 5

Fruit fiber mixture with chitosan

| Ingredient | Amount (parts/100) |
| --- | --- |
| Apple fiber powder | 20 |
| Chitosan | 60 |
| Anticaking and flow enhancing agents | 8 |
| Flavors and sweeteners | 12 |

The proportion of chitosan to other dietary fiber in this Example is 3:1 and the weight percentage of chitosan to total weight of the composition is 60 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 6

Vegetable fiber mixture with chitosan

| Ingredient | Amount (parts/100) |
| --- | --- |
| Beet fiber powder | 30 |
| Chitosan | 50 |
| Anticaking and flow enhancing agents | 8 |
| Flavors and sweeteners | 12 |

The proportion of chitosan to other dietary fiber in this Example is 5:3 and the weight percentage of chitosan to total weight of the composition is 50 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 7

Psyllium hydrocolloid mixture with chitosan

| Ingredient | Amount (parts/100) |
| --- | --- |
| Psyllium seed, husk, or hydrocolloid powder | 40 |
| Chitosan | 40 |
| Anticaking and flow enhancing agents | 8 |
| Flavors and sweeteners | 12 |

The proportion of chitosan to other dietary fiber in this Example is 1:1 and the weight percentage of chitosan to total weight of the composition is 40 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

EXAMPLE 8

Legume fiber mixture with chitosan

| Ingredient | Amount (parts/100) |
| --- | --- |
| Soybean fiber powder | 60 |
| Chitosan | 20 |
| Anticaking and flow enhancing agents | 8 |
| Flavors and sweeteners | 12 |

The proportion of chitosan to other dietary fiber in this Example is 1:3 and the weight percentage of chitosan to total weight of the composition is 20 percent.

When granulated and mixed together and tabletted or filled into capsules, or suspended in water as a drink mix with a suitable suspending or emulsifying agent according to established knowledge of the art, the results upon oral administration are essentially as found for the composition of Example 1 and reported under "Pharmacology".

PHARMACOLOGY

According to the Tomlin, Lowis, and Read study entitled "Investigation of normal flatus production in healthy volunteers", Gut 32: 665–669 (1991), the average healthy adult experiences flatus eight (8) times a day, releasing a median volume of ninety (90) ml of expelled gas with each flatus. Therefore, to determine a baseline for a one-week period, a record was kept of the flatus experience of a healthy adult male. As a baseline for the one-week period, the average daily flatus was determined to be eight (8), with the range being 3–13.

To this healthy volunteer was administered a six (6) gram dose of the product of Example 1 hereof three (3) times a day, with the only exception that a 1:1:1 mixture of acacia gum, pectin, and guar gum was first substituted for the composition of Example 1, to first make a control determination in the absence of chitosan. The composition was administered orally mixed with eight (8) ounces of water three (3) times per day for one (1) week. A record of the daily flatus experienced was maintained, the average increasing to 21 per day, the range being 6–41.

After a two-week washout period to give the healthy volunteer an opportunity to return to baseline, a six (6) gram dose of the exact composition of Example 1, including the chitosan, was taken three (3) times a day, admixed with the same amount of water, over a one-week period. Upon oral administration of the composition of Example 1, including the chitosan, there was no increase in the daily number of flati, the average again being eight (8) with a range of 5–12. Without exact measurement of the volume of expelled gas during the test periods, it was the subjective impression of the healthy volunteer that the volume of gas expelled during the period of fiber without chitosan testing was substantially greater than for the other two (2) test periods involved.

Incorporation of the test materials in a usual gelatin capsule for oral ingestion, or administration of the flatulence-reducing amount of chitosan concurrently with the other dietary fibers, is productive of essentially the same results in the pharmacological testing, namely, reduction in the number and amount of flatuli when the flatulence-reducing amount of chitosan is orally ingested in admixture with other dietary fiber components or administered concurrently therewith.

REFERENCES

1. M. J. Koruda. Dietary fiber and gastrointestinal disease. Surg. Gynecol. Obstret. 177:209–214 (1993).
2. C. E. Day and E. Kuhrts. Method and composition for reducing serum cholesterol. U.S. Pat. No. 4,824,672 (1989).
3. C. E. Day and E. Kuhrts. Method and composition for reducing serum cholesterol. U.S. Pat. No. 4,883,788 (1989).
4. J. Tomlin, C. Lowis, and N. W. Read. Investigation of normal flatus production in healthy volunteers. Gut 32: 665–669 (1991).
5. E. W. Hellendoorn. Fermentation as the principal cause of the physiological activity of indigestible food residue. In: Topics in Dietary Fiber Research ed. by G. A. Spiller and R. J. Amen, Plenum Press, New York, N.Y., pp. 127–168 (1978).
6. T. G. Ganiats, W. A. Norcross, A. L. Halverson, P. A. Burford, and L. A. Palinkas. Does Beano prevent gas? A double-blind crossover study of oral α-galactosidase to treat dietary oligosaccharide intolerance. J. Fam. Pract. 39: 441–445 (1994).
7. M. Sugano, T. Fujikawa, Y. Hiratsuji, and Y. Hasegawa. Hypocholesterolemic effects of chitosan in cholesterol-fed rats. Nutr. Rep. Internat. 18: 531–537 (1978).
8. Y. Maezaki, K. Tsuji, Y. Nakagawa, Y. Kawai, M. Akimoto, T. Tsugita, W. Takekawa, A. Terada, H. Hara, and T. Mitsouka. Hypocholesterolemic effect of chitosan in adult males. Biosci. Biotech. Biochem. 57: 1439–1444 (1993).
9. Y. Fukada, K. Kimura, and Y. Ayaki. Effect of chitosan feeding on intestinal bile acid metabolism in rats. Lipids 26: 395–399 (1991).

10. I. Furda. Nonabsorbable lipid binder. U.S. Pat. No. 4,223,023 (1980).
11. O. Kanauchi and K. Deuchi. Dietary lipid digestion-absorption inhibitory agents and ingesta. U.S. Pat. No. 5,453,282 (1995).
12. S. Ace, H. Oda, and K. Tatsumi. Water-soluble dietary fiber-chitosan complexes for use in food. Jpn. Kokai Tokkyo Koho JP 05 86,227 [93,86,227]. (Chem. Abstr. 119: 141508 (1993)).
13. A. H. M. Ross, M. A. Eastwood, W. G. Brydon, J. R. Anderson, and D. M. W. Anderson. A study of the effects of dietary gum arabic in humans. Amer. J. Clin. Nutr. 37: 368–375 (1983).
14. M. Meshali and K. Gabr, Effect of interpolymer complex formation of chitosan with pectin or acacia on the release behavior of chlorpromazine hydrochloride. International Journal of Pharmaceutics (Amsterdam) 89(3), 177–181 (1993).
15. M. Tanaka, T. Toshima, and K. Tatsumi, Manufacture of dietary fiber-rich expanded foods with chitosan. Jpn. Kokai Tokkyo Koho JP 03 262 461 [91,262,461]. (Chem. Abstr. 116: 104868u (1992)).
16. C. E. Day, Method for treatment of irritable bowel syndrome. U.S. Pat. No. 5,380,522 (1995).
17. J. L. Nelson, J. W. Alexander, L. Gianotti, C. L. Chalk, and T. Pyles. Influence of dietary fiber on microbial growth in vitro and bacterial translocation after burn injury in mice. Nutrition 10: 32–36 (1994).
18. L. A. Hadwiger, T. Ogawa, and H. Kuyama. Chitosan polymer sizes effective in inducing phytoalexin accumulation and fungal suppression are verified with synthesized oligomers. Mol. Plant Microbe Interact. 7: 531–533 (1994).
19. A. Terada, H. Hara, D. Sato, T. Higashi, S. Nakayama, K. Tsuji, K. Sakamoto, E. Ishioka, Y. Maezaki, T. Tsugita, T. Takekawa, and T. Mitsuoka. Effect of dietary chitosan on faecal microbiota and faecal metabolites of humans. Microb. Ecol. Health Dis. 8: 15–21 (1995).

It is therefore seen that the present invention provides a unique dietary fiber formulation, consisting of the following essential ingredients: A gel-forming dietary fiber, usually in an amount effective to produce an antihypercholesterolemic effect, plus, in addition to other dietary fibers, a flatulence-reducing amount of chitosan, plus optional anticaking and flow-enhancing agents, flavors, and sweeteners, as set forth in the foregoing, and particularly and advantageously a plurality of dietary fibers other than chitosan as set forth in Example 1 hereof. Additionally, the method of producing a dietary fiber formulation which produces reduced flatulency upon oral administration to a living animal body, especially a human being, which includes the step of incorporating in the dietary fiber composition, in addition to other dietary fiber components thereof, a flatulence-reducing amount of chitosan or, alternatively, administering such a flatulence-reducing amount of chitosan concurrently with the other dietary fiber constituents. Furthermore, a method of reducing flatulency upon oral administration of a dietary fiber composition to a human being which includes the step of administering concurrently or in admixture with the other dietary fiber components of the composition a flatulence-reducing amount of chitosan, all of the foregoing aspects of the present invention having the unpredictable and highly advantageous characteristics and effect as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A method of reducing flatulence which results upon oral ingestion by a human being of an orally-ingestible dietary fiber other than chitosan, comprising the step of (a) admixing a flatulence-reducing amount of chitosan with the dietary fiber other than chitosan before oral ingestion thereof and (b) orally ingesting the admixture of step (a).

2. The method of claim 1, wherein the dietary fiber other than chitosan is selected from the group consisting of acacia gum, pectin, guar gum, beta-glucan, fruit fibers, vegetable fibers, legume fibers, psyllium, plantago, xanthan, agar, alginic acid, cellulose gum, methylcellulose, agarose, dextran, tragacanth, karaya, glucomannan, locust bean, konnyaku mannan, and carrageenan.

3. The method of claim 1, wherein a plurality of dietary fibers other than chitosan are admixed and ingested.

4. The method of claim 1, wherein the weight ratio of chitosan, which is admixed with other dietary fibers, to the other dietary fibers is between about 1:20 and about 10:1.

5. The method of claim 1; wherein the weight ratio of chitosan to other dietary fibers is between about 1:17 and about 3:1.

6. The method of claim 1, wherein the weight ratio of chitosan to other dietary fibers is between about 1:10 and about 1:4.

7. The method of claim 1, wherein the percent by weight of chitosan in the total dietary fiber admixture is between about 5 and about 90.

8. The method of claim 1, wherein the percent by weight of chitosan in the total admixture is between about 10 and about 60.

9. The method of claim 1, wherein the percent by weight of chitosan in the total admixture is between about 10 and about 25.

10. The method of reducing flatulence which results upon oral ingestion by a human of an orally-ingestible dietary fiber other than chitosan, comprising the step of orally ingesting a flatulence-reducing amount of chitosan in admixture with or concurrently with the dietary fiber other than chitosan.

11. The method of claim 10, wherein the weight ratio of chitosan to other dietary fibers ingested is between about 1:20 and about 10:1.

12. The method of claim 10, wherein the weight ratio of chitosan to other dietary fibers is between about 1:17 and about 3:1.

13. The method of claim 10, wherein the weight ratio of chitosan to other dietary fibers is between about 1:10 and about 1:4.

14. The method of claim 10, wherein the percent by weight of chitosan to the total amount of dietary fiber composition ingested is between about 5 and about 90.

15. The method of claim 10, wherein the percent by weight of chitosan to the total amount of dietary composition ingested is between about 10 and about 60.

16. The method of claim 10, wherein the percent by weight of chitosan to the total amount of dietary composition ingested is between about 10 and about 25.

17. The method of claim 10, wherein the dietary fiber other than chitosan is selected from the group consisting of acacia gum, pectin, guar gum, beta-glucan, fruit fibers, vegetable fibers, legume fibers, psyllium, plantago, xanthan, agar, alginic acid, cellulose gum, methylcellulose, agarose, dextran, tragacanth, karaya, glucomannan, locust bean, konnyaku mannan, and carrageenan.

18. The method of claim 10, wherein a plurality of dietary fibers other than chitosan are ingested.

* * * * *